United States Patent [19]
Poynter

[11] Patent Number: 5,509,906
[45] Date of Patent: Apr. 23, 1996

[54] PLUNGERLESS SYRINGE

[75] Inventor: Richard Q. Poynter, Palm Beach, Fla.

[73] Assignee: HealthStar Pharmaceutical Services, Inc., Riviera Beach, Fla.

[21] Appl. No.: 431,686

[22] Filed: May 2, 1995

[51] Int. Cl.$^6$ .................................................. A61M 1/00
[52] U.S. Cl. ............................................ 604/212; 604/216
[58] Field of Search ................................ 604/212–216, 604/187, 217, 227

[56] References Cited

U.S. PATENT DOCUMENTS

| | | | |
|---|---|---|---|
| 3,473,524 | 10/1969 | Drewe | 604/216 |
| 3,844,284 | 10/1974 | Schoenfeld et al. | 604/216 |
| 4,411,656 | 10/1983 | Cornett, III | 604/212 |
| 4,753,638 | 6/1988 | Peters | 604/212 |
| 5,242,422 | 9/1993 | Schneberger et al. | 604/212 X |

*Primary Examiner*—John D. Yasko
*Attorney, Agent, or Firm*—Samuels, Gauthier & Stevens

[57] ABSTRACT

A plungerless syringe which comprises a collapsible body having a sealed dispensing tip at one end and an actuating tab at the other end. The collapsible body is characterized by a plurality of rings concentrically arrayed on the surface of the body wall. When the actuating tab is depressed the body commences to collapse and a first ring is received within and frictionally engages a second succeeding ring and remains secured thereto.

3 Claims, 1 Drawing Sheet

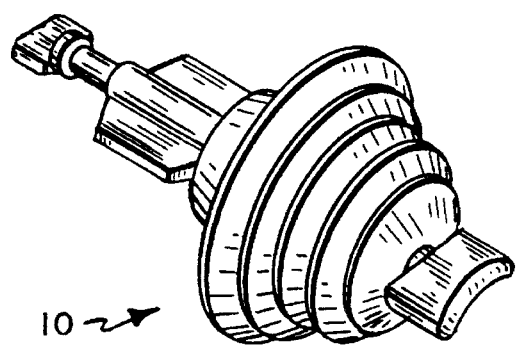
FIG. 1
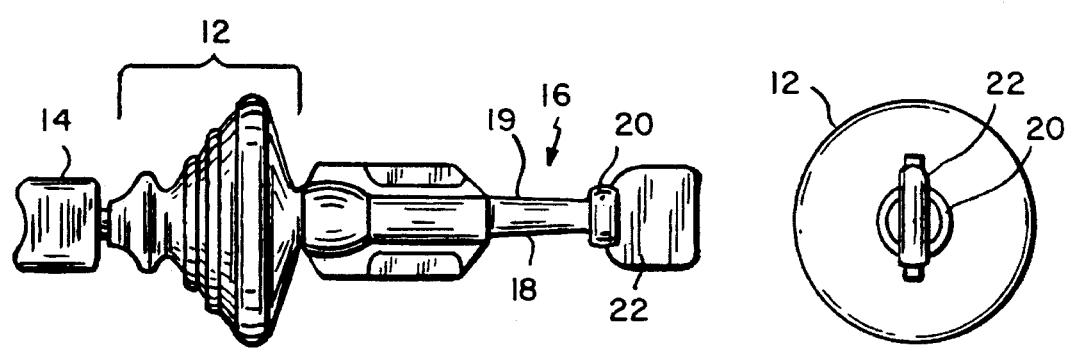
FIG. 2    FIG. 4
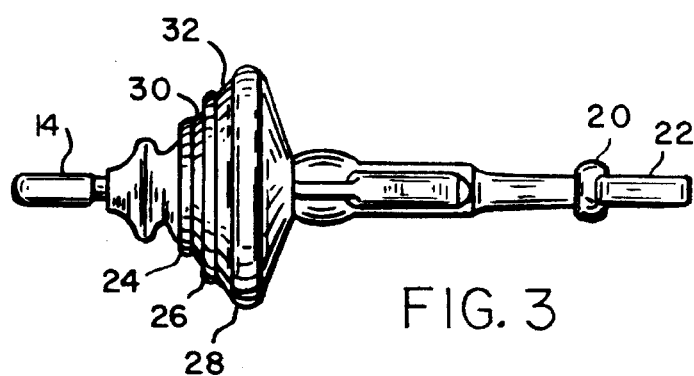
FIG. 3
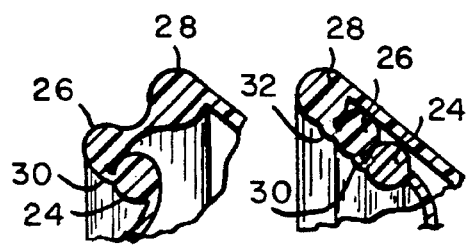
FIG. 5b    FIG. 5c
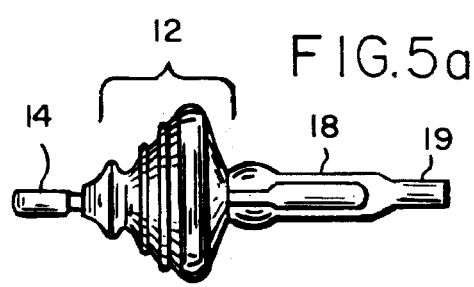
FIG. 5a
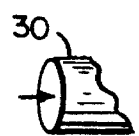

PLUNGERLESS SYRINGE

FIELD OF THE INVENTION

The invention relates to syringes used in the health care field.

BACKGROUND AND BRIEF SUMMARY OF THE INVENTION

In the health care field, syringes have different functions. The primary function is to introduce and/or withdraw fluids into and from the body. The introduction of fluids into the body typically requires precise metering and the syringes are relatively expensive because of the close tolerances required between the plunger of the syringe and the sleeve within which it reciprocates. The withdrawal of fluids from the body may not require precise metering but usually the same, relatively expensive, syringe will be used simply as a matter of convenience.

Another function of syringes is the flushing of catheters and the like which catheters are in situ. An anti-coagulant, such as herapin, flushes the catheter which is subsequently aspirated to ensure that the catheter is still functioning properly. Syringes used for this purpose do not need to precisely meter the fluid into the body and therefore, the close tolerances required of those syringes specifically used for introducing a fluid into the body are not required.

The present invention relates to a syringe which, in effect, is plungerless and which can deliver predetermined amounts of fluid, such as an anti-coagulant, into a catheter or the like instrument.

Broadly the invention comprises a sealed syringe having a collapsible body. The syringe comprises a dispensing tip and an actuating tab. The syringe is formed, filled with a metered amount of fluid and sealed. The collapsible body is characterized by a plurality of steps or ribs which engage one another when the body is collapsed. The steps allow the body to be collapsed in an index or calibrated manner.

In a preferred embodiment, the collapsible body is bell-shaped and the steps comprise a plurality of concentrically arrayed ribs formed in seriatim on the outer surface of the body. The ribs define walls or membrane sections therebetween. When the body is collapsed, one rib is telescopically received and secured within the next succeeding rib. The telescoped ribs ensure the body stays in its collapsed position. If fluids are to be aspirated from the body, the dispensing tip remains in situ and the actuating tab is withdrawn and the ribs are released from one another. The movement of one rib within another is smooth, not unlike a piston sliding into a cylinder. This ensures a constant even pressure in dispensing the fluid. It prevents surges and the creation of back-pressure which would cause uneven flow.

BRIEF DESCRIPTION OF THE DRAWINGS

FIG. 1 is a perspective view of a syringe embodying the invention;

FIG. 2 is a side elevation of the syringe of FIG. 1;

FIG. 3 is a top elevation of the syringe of FIG. 1;

FIG. 4 is an end view of the syringe of FIG. 1; and

FIGS. 5a, 5b and 5c are illustrations of the operation of the plungerless syringe.

DESCRIPTION OF THE PREFERRED EMBODIMENT(S)

Referring to FIGS. 1, 2, 3 and 4 the invention comprises a syringe 10 having a collapsible chamber 12. At one end of the chamber 12 is an actuating tab 14 and at the other end is a dispensing assembly 16.

The dispensing assembly 16 comprises an elongated tubular passageway 18, terminating in a tapered end 19 sealed by a dispensing tip 20 to which is joined a tear tab 22.

The chamber 12 is cone-shaped with the base of the cone joined to the dispensing assembly 16. The chamber comprises a plurality of circular ribs 24, 26 and 28 concentrically arrayed along the longitudinal axis of the syringe. The ribs are dimensioned such that they are adapted to be telescopically received within one another, in succession, in smooth gliding, frictional engagement. The ribs define flexible walls 30 and 32 which allow the ribs to telescope into and out of a collapsed and an extended position.

In the operation of the invention, referring to FIGS. 5a, 5b and 5c, the tip 20 on the dispensing assembly 16 is removed and the tip 19 inserted in a catheter 30, this is shown in FIG. 5a. Pressure is applied to the actuating tab 14 and as shown in FIG. 5b the wall 30 flexes and the rib 24 is smoothly received in the rib 26. The dimensioning of the collapsible body is such that the rib 26 is held in frictional engagement by the rib 28. This also ensures that no fluid backfills into the upper portion of the collapsible body when pressure is applied to the actuating tab 14. As shown in FIG. 5c, the body is fully collapsed, the rib 26 being received within the rib 28. Again, the ribs are received within one another to provide an effective seal against backfill of the fluid in the syringe thus ensuring dispensing of accurate amounts of fluid. The plungerless syringe will remain in the collapsed position until pressure is applied to the actuating tab 14 to withdraw the rings one from the other thereby applying a suction to the dispensing tip 19.

The invention has been described with reference to three ribs and a fluid-filled body adapted to be collapsed to an intermediate position where a certain amount of fluid is dispensed, and into a final position wherein the total amount of fluid is dispensed.

In the preferred embodiment of the invention, the amount of fluid dispensed in the first and second steps (FIGS. 5b and 5c) will depend upon the specific geometry of the plunger. It is within the skill of the art to design the chamber such that when it moves to one or more intermediate positions (by the addition of further rings or steps) that a desired amount of fluid be metered. For example, if a syringe of the invention contained 500 cc, then it can be designed such that at the first step 250 cc be dispensed and at the second step the remaining 250 cc be dispensed. It being understood that even when the plunger is fully in the collapsed position, there will be some fluid remaining in the dispensing assembly per se. That is, if a syringerless plunger of the invention is designed for a total dispensation of 500 cc it would be filled with slightly excess 500 cc to account for the fluid remaining in the dispensing tip.

It is well within the skill of the blow/fill/seal art that other means for indexing the amount of fluid dispensed may be used. Further, the syringe material of construction is essentially transparent such that if the syringe is aspirated to ensure that a catheter passageway has been flushed it will enable the user to view the blood returning into the syringe when it is aspirated.

Although described in reference to syringes, the invention concepts are applicable generally to blow/fill/seal dispensers, i.e. bottles.

The foregoing description has been limited to a specific embodiment of the invention. It will be apparent, however, that variations and modifications can be made to the invention, with the attainment of some or all of the advantages of the invention. Therefore, it is the object of the appended claims to cover all such variations and modifications as come within the true spirit and scope of the invention.

Having described my invention, what I now claim is:

1. A plungerless syringe which comprises:

a collapsible body having a wall containing fluid to be dispensed, a sealed dispensing tip secured to the body, means secured to the body to apply pressure to the body and means to control the collapse of the body which means comprises a plurality of rings, the rings concentrically arrayed on the surface of the body wall, a first ring adapted to be received within and frictionally secured to a second succeeding ring when the body is collapsed and to remain releasably secured thereto.

2. The syringe of claim 1 wherein the sealed dispensing tip is tapered having a larger end and a smaller end, the larger end joined to the body, the other end characterized by a dispensing tab which seals the dispensing tip.

3. The syringe of claim 1 wherein the means secured to the body to apply pressure to the body comprises an actuating tab.

* * * * *